United States Patent [19]
Triozzi et al.

[11] Patent Number: 6,093,381
[45] Date of Patent: *Jul. 25, 2000

[54] MODULATION OF THE SENSITIVITY OF TUMOR CELLS TO CHEMOTHERAPEUTICS

[75] Inventors: Pierre L. Triozzi; Julian A. Kim, both of Columbus, Ohio

[73] Assignee: Neoprobe Corporation, Dublin, Ohio

[ * ] Notice: This patent is subject to a terminal disclaimer.

[21] Appl. No.: 08/988,341

[22] Filed: Dec. 10, 1997

Related U.S. Application Data

[63] Continuation-in-part of application No. 08/271,902, Jul. 13, 1994, Pat. No. 5,814,295.
[51] Int. Cl.[7] .......................... A61K 51/00; A61K 31/00; A61K 39/40; A61K 39/395
[52] U.S. Cl. .......................... 424/1.49; 424/1.49; 424/9.1; 424/9.322; 424/1.41; 424/1.17; 424/93.7; 424/85.1; 424/85.2; 424/93.1; 424/155.1; 424/152.1; 424/520; 424/534; 435/372.2
[58] Field of Search ...................................... 424/1.49, 9.1, 424/9.322, 1.41, 1.17, 93.7, 85.1, 85.2, 93.1, 155.1, 152.1, 520, 534; 435/372.2

[56] References Cited

U.S. PATENT DOCUMENTS

| | | |
|---|---|---|
| 4,741,900 | 5/1988 | Alvarez et al. . |
| 4,782,840 | 11/1988 | Martin et al. . |
| 5,041,289 | 8/1991 | Phillips et al. . |
| 5,071,872 | 12/1991 | Witiak et al. . |
| 5,126,132 | 6/1992 | Rosenberg et al. . |
| 5,814,295 | 9/1998 | Martin et al. . |
| 5,859,065 | 1/1999 | Brandes et al. . |
| 5,876,735 | 3/1999 | Reed . |
| 5,882,626 | 3/1999 | Epstein et al. . |
| 5,965,132 | 10/1999 | Thorpe et al. . |

FOREIGN PATENT DOCUMENTS 2128175 of 1995 Canada .

OTHER PUBLICATIONS

Rhinehart et al, Clinical Cancer Research 1:1139–1144, 1995.

Kim et al, Cancer, 86:22–30, 1999.

Yoshizawa et al J. Immunol 147/2:729–737, Jul. 1991.

Merecki et al J. Biol. Response Modifiers 9:463–474, 1990.

Friozzi et al. Cancer 73:580–589, 1994.

Steele et al. JAMA, 264/11:1444–1450, 1990.

Kim et al, J. Immunother. 14/4:366 Abstract only, 1993.

Kawata et al. Am. J. Clin. Oncol. (CCT) 18/3:257–262, 1995.

Rinehart et al. Cancer Investigation 15/5:403–410, 1997.

Klefstrom et al. Acta Radiologica Oncology 25/3:161–166, 1986.

*Primary Examiner*—Nita Minnifield
*Attorney, Agent, or Firm*—Mueller and Smith, LPA

[57] ABSTRACT

Disclosed is a method for improving the treatment of a cancer patient which is undergoing (adjuvant) chemotherapy. Prior to or concomitant with the patient receiving adjuvant chemotherapy, the patient is administered mitogenically stimulated lymph node lymphocytes or the supernatant therefrom. The lymph node lymphocytes are patient excised lymph node lymphocytes enriched in tumor reactive cells, such as CD4+ tumor reactive cells. Radiolabeled locators (e.g., antibodies) can be used along with a portable radiation detector to intraoperatively determine which lymph nodes bear lymph node lymphocytes enriched in tumor reactive cells. The patient excised lymph node lymphocytes enriched in tumor reactive cells then are subjected to mitogenic stimulation for their expansion and administration to the patient.

20 Claims, 13 Drawing Sheets

MODULATION OF THE SENSITIVITY OF TUMOR CELLS TO CHEMOTHERAPEUTICS

CROSS-REFERENCE TO RELATED APPLICATIONS

This application is a continuation-in-part of application Ser. No. 08/271,902, filed on Jul. 13, 1994, now U.S. Pat. No. 5,814,295, the disclosure of which is expressly incorporated herein by reference.

STATEMENT REGARDING FEDERALLY SPONSORED RESEARCH

Not applicable.

BACKGROUND OF THE INVENTION

The present invention relates generally to the treatment of cancer with chemotherapeutic agents and more specifically to enhancing their effect.

In co-pending application Ser. No. 08/271,902 now U.S. Pat. No. 5,814,295 disclosed are therapeutic agents effective in mitigating tumor progression which agents include a carrier and lymphocyte cells that have been produced by mitogenically stimulating patient excised lymph nodes enriched in tumor-specific lymphocytes enriched in tumor reactive cells, e.g., $CD_4+$ tumor specific lymphocytes. Lymph nodes enriched in tumor-specific lymphocytes comprising $CD_4+$ tumor specific lymphocytes were determined by administering a radiolabeled locator to a patient, surgically accessing the patient and locating such lymph nodes with a hand-held radiation detector, and removing the nodes that visually do not contain evidence of tumor. These lymph node lymphocytes are cultured under mitogenic conditions to form the therapeutic agents of interest.

Based on the response reported in patient 4 in application Ser. No. 08/271,902 now U.S. Pat. No. 5,814,295 the inventors stated that subjecting the patients that have received the therapeutic agent of that invention to adjuvant chemotherapy may be of particular benefit to the patient; even to those patients that were recalcitrant to chemotherapy prior to receiving the inventive adoptive cellular therapy treatment disclosed therein. This is particularly important in view of the National Institutes of Health (NIH) consensus report concerning the administration of adjuvant chemotherapy to appropriately staged patients. "NIH Consensus Conference: Adjuvant Therapy for Patients with Colon and Rectal Cancer", JAMA, 1990; 264:1444–50.

In view of the reported findings cited above, the effects of soluble products secreted by the tumor-reactivated lymphocytes expanded from patients with an adenocarcinoma (colorectal cancer) on the chemosensitivity of colorectal tumor cells in vitro were examined in greater depth. The results of these studies is the basis for the present invention.

BRIEF SUMMARY OF THE INVENTION

Disclosed is a method for improving the treatment of a cancer patient which is undergoing (adjuvant) chemotherapy. Prior to or concomitant with the patient receiving adjuvant chemotherapy, the patient is administered the supernatant from lymph node lymphocytes cultured under mitogenic stimulation conditions or the cultured lymph node lymphocytes themselves. The lymph node lymphocytes are patient excised lymph node lymphocytes enriched in tumor reactive cells, such as CD4+ tumor reactive cells. Radiolabeled locators (e.g., antibodies) can be used along with a portable radiation detector to intraoperatively determine which lymph nodes bear lymph node lymphocytes enriched in tumor reactive cells. The patient excised lymph node lymphocytes enriched in tumor reactive cells then are subjected to mitogenic stimulation for their expansion and administration of their supernatant to the patient.

Another aspect of the present invention is a method for improving the activity of chemotherapeutic agents. This method comprises combining a chemotherapeutic agent with the supernatant of lymph node lymphocytes cultured under mitogenic stimulation conditions or the cultured lymph node lymphocytes themselves. The lymph node lymphocytes are cancer patient excised lymph node lymphocytes enriched in tumor reactive cells. Thus, the supernatant of the present invention is co-administered (i.e., prior to or concomitant therewith) with chemotherapeutics.

Advantages of the present invention include the administration of a therapeutic agent (the supernatant) which causes no adverse side effects to the patient. Another advantage is the possibility that less chemotherapy may be required by dint of the supernatant being used in combination therewith. A further advantage is that the supernatant alone has been shown to display therapeutic benefit sans the chemotherapeutic. These and other advantages will be apparent to those skilled in the art based on the disclosure herein.

DETAILED DESCRIPTION OF THE INVENTION

Figure 1:
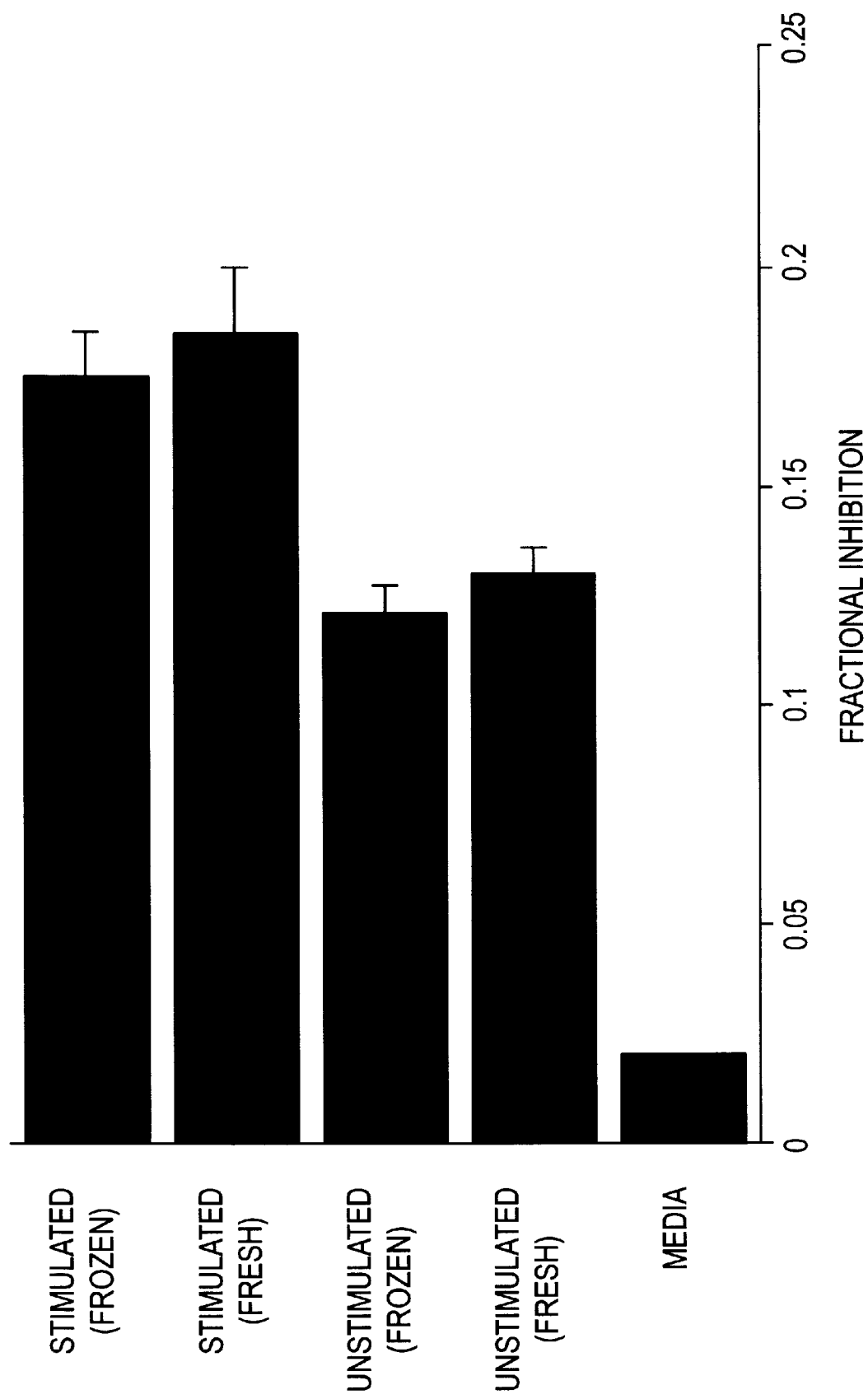
FIG. 1 depicts the antiproliferative activity of Unstimulated and Stimulated supernatants that had been freshly collected or frozen and of the expansion media supplemented with IL-2 (Media) added at 25% (v/v) to LS 174T cells in culture. Data represent mean ± SD (standard deviation) for three different supernatants.

Combining immunotherapeutics with cytotoxic drugs is an attractive approach to increase the therapeutic index in neoplastic diseases. At present, there is no consensus on an optimal strategy. Kreuser, et al., "Biochemical modulation of cytotoxic drugs by cytokines: molecular mechanisms in experimental oncology", *Recent Results Cancer Res*, 139:371–82, 1995. Adoptive cellular immunotherapy has been effectively combined with chemotherapeutics in pre-clinical studies designed to exploit the capacity of the chemotherapeutic to enhance the activity of cytolytic lymphocytes and/or exploit the observation that drug-resistant tumor may still be sensitive to cytolytic lymphocytes. See Gazit, et al., "Chemo-adoptive immunotherapy of nude mice implanted with human colorectal carcinoma and melanoma cell lines", *Cancer Immunol Immunother*, 35:135–44, 1992) and Treichel, et al., "The relationship between multi-drug resistance and resistance to natural-killer-cell and lymphokine-activated killer-cell lysis in human leukemia cell lines", *Int J Cancer*, 50:305–310, 1992. Translating these interactions to the clinic has been difficult, and results in clinical trials have been disappointing. Kawata, et al., "Adjuvant chemoimmunotherapy for hepatocellular carcinoma patients. Adriamycin, interleukin- 2, and lymphokine-activated killer cells versus adriamyacin alone", *Am J Clin Oncol*, 18:157–62, 1995.

Work done on the present invention evidences another potential mechanism of beneficial interaction between lymphocytes and chemotherapeutics which mechanism does not directly involve the cytolytic activity of lymphocytes, but rather their secretory activity. This work points to the products of non-cytolytic, tumor-reactive lymphocytes expanded from patients with colorectal cancer which products can enhance the sensitivity of colorectal tumor cells in vitro to a variety of cytotoxic chemotherapeutics. At least one patient has evidenced a response to chemotherapy following practice of the present invention even though the patient was recalcitrant to chemotherapy prior thereto.

The molecular mechanisms underlying the interaction are not clear. The broad spectrum of cytotoxic drugs whose activity can be enhanced argues for multiple levels of interaction. The expanded lymphocytes secrete a variety of cytokines which have been shown to modulate the growth and/or sensitivity of colorectal cancer cells to cytotoxic chemotherapeutics, including, for example: TNFα, IFNγ, IL-4, and GM-CSF. Schiller, et al., "Anti-proliferative effects of tumor necrosis factor, gamma interferon and 5-fluorouracil on human colorectal carcinoma cell lines", *Int J Cancer*, 46(1):61–6, 1990); Chu, et al., "The interactions of γ interferon and 5-fluorouracil in the H630 human carcinoma cell line, *Cancer Res*, 50:5834–5840, 1990; Lahm, et al., "Grown inhibition of human colorectal-carcinoma cells by interleukin-4 and expression of functional interleukin-4 receptors", *Int J Cancer*, 59:440–447, 1994; and Berdel, et al., "Stimulation of clonal growth of human colorectal tumor cells by IL-3 and GM-CSF. Modulation of 5-FU cytotoxicity by GM-CSF", *Onkologie*, 13:437–443, 1990. Whether the effects are mediated by cytokines, however, has not yet been established in the literature, and it is possible that other soluble mediators are operational.

As the supernatants alone inhibit tumor cell growth and decrease the number of cells in the S phase, the enhancement of chemosensitivity is not the result of recruiting cells into the cell cycle. In this regard, the one agent in which antagonistic interactions were observed was Gemcitabine, an S-phase specific drug. Modulation of drug target enzyme, change in metabolism or disposition of a drug, and alteration in the cellular drug uptake are possible mechanisms.

Synergistic antiproliferative activity was observed in most cell lines with 5-FU, the most active agent in clinical use in colorectal cancer. The capacity of IFN to enhance 5-FU cytotoxicity is well established. Like the supernatants studied, IFN has demonstrated antiproliferative activity against cells in vitro, which argues against the recruitment of $G_0$ cells into the cell cycle in the interaction with the S-phase-specific 5- FU. Mechanisms involved in the synergistic interaction of IFN and 5-FU appear to be the increase of active 5-FU metabolites by IFN and a decrease in the uptake of thymidine to inhibit a salvage pathway. Moreover, IFN can reverse resistance against 5-FU by inhibiting the over-expression of thymidylate synthetase. Lahm, et al, "Growth inhibition of human colorectal-carcinoma cells by interleukin-4 and expression of functional interleukin-4 receptors", supra; Wadler, et al., "Influence of cytokines on mdrl expression in human colon carcinoma cell lines: increased cytotoxicity of MDR relevant drugs", *J Cancer Res Clin Oncol*, 120:471–478, 1994.

Work on the present invention has demonstrated a decrease in thymidylate synthese niRNA using a semi-quantitative PCR method in LS513 cells, but not in LS 174T and SW480 cells. Whether protein expression or catalytic activity actually was modulated was not assessed.

The supernatants were shown to enhance the activity of agents that interact with topoisomerase, which has emerged as a critical intracellular target of cytotoxic drugs in several cancers, including colorectal cancer. The antiproliferative activity of both topoisomerase-I interactive, e.g., Irintotecan, and topoisomerase-II interactive, e.g., Doxorubicin and Etoposide, agents were enhanced. There is evidence that the synergy between TNF and topoisomerase-targeted drugs is related to a rapid increase in specific activity of topoisomerase I and II, resulting in enhanced DNA strand breaks and cleavage complex. Kreuser, et al., "Biochemical modulation of cytotoxic drugs by cytokines: molecular mechanisms in experimental oncology", supra.

Cytokines also have been shown to modulate the activity of P-glycoprotein, transmembrane efflux pump encoded by the mdr-1 gene, which has been implicated in the resistance of tumor to many cytotoxic drugs. Walther. et al., "Influence of cytokines on mdrl expression in human colon carcinoma cell lines: increased cytotoxicity of MDR relevant drugs", supra. The increased uptake in Doxorubicin effected by the supernatants suggests the possibility that this mechanism may be modulated.

The role of tumor-reactive lymphocytes in the regulation of colorectal cancer growth in vivo is not known. Although the significance has not been clearly established, there are data that suggest that the infiltration of colorectal tumors by lymphocytes confers a more favorable prognosis. Di Giorgio, et al., "The influence of tumor lymphocytic infiltration on long term survival of surgically treated colorectal cancer patients", *Int Sur,* 77:256–260, 1992. Lymphocytes infiltrating colorectal cancers have low proliferative and cytolytic capacity, but have been shown to secrete normal levels of cytokines, such as IFNg. Bateman, et al., "Lymphocytes infiltrating colorectal cancer have low proliferative capacity but can secrete normal levels of interferon gamma", *Cancel Immunol Immunother,* 41:61–7, 1995.

Immune effector cell function is preserved following administration of 5-FU, even at high doses. Weiner, et al., "Preservation of immune effector cell function following administration of a dose-intense 5-fluorouracil-chemotherapy regimen", *Cancel Immunol Immunother,* 36:185–90, 1993. Thus, it is possible that the more favorable prognosis manifested in patients with significant infiltration of lymphocytes into their tumors may be a consequence of an enhanced sensitivity to the 5-FU-based chemotherapy applied to these individuals. Although several cytokines have demonstrated a capacity to increase the sensitivity of tumor cells to cytotoxic agents, prolonged, high, local concentrations appear to be necessary. Walther. et al., "Influence of cytokines on mdrl expression in human colon carcinoma cell lines: increased cytotoxicity of MDR relevant drugs", supra; Borsellino, et al., "Combined activity of interleukin-1 alpha or TNF-alpha and Doxorubicin on multi-drug resistance cell lines: evidence that TNF and DXR have synergistic antitumor and differentiation-inducing effects", *Anticancer Res,* 14:264–268, 1994; Stein, et al., "Modulation of mdrl expression by cytokine in human colon carcinoma cells: an approach for reversal of multi-drug resistance", *Br J Cancer,* 74:1384–1391, 1996.

The clinical toxicities of achieving these with most agents would be predicted to be limiting. Intratumoral and locoregional treatments, including transduction of cytokine genes, have been considered but have the obvious limitation of delivery to metastatic tumor. Stein, et al., "Reversal of multi-drug resistance by transduction of cytokine genes into human colon carcinoma cells", *J Natl Cancer Inst,* 88:1383–1392, 1996. Infusing cytokine-secreting lymphocytes, which have virtually no toxicity, with cytotoxic drugs offers a new approach to increase the therapeutic index in the treatment of neoplastic diseases. Theoretically, the lymphocytes could traffic to tumor and release cytokines in a regulated, paracrine fashion. The nature of the active factors and whether they are released in sufficient quantities in vivo is not yet fully known. Furthermore, the present work does not indicate variability in the sensitivity of colorectal tumor cells. Finally, interaction in vivo between cells and cytotoxic agents involves additional layers of complexity because of, e.g., the effects of cytokines on the host immune system and on drug-metabolizing enzymes. Nevertheless, the present work clearly shows a dramatic effect on chemotherapeutics by use of the mitogenically stimulated lymph node lymphocytes according to the present invention.

The first step of the method of the present invention comprises the administration to the patient of an effective amount of a radiolabeled locator which specifically binds a marker produced by or associated with neoplastic tissue. As stated above, a "locator" includes a substance which preferentially concentrates at the tumor sites by binding with a marker (the cancer cell or a product of the cancer cell, for example) produced by or associated with neoplastic tissue or neoplasms. Appropriate locators today primarily include antibodies (whole and monoclonal), antibody fragments, chimeric versions of whole antibodies and antibody fragments, and humanized versions thereof. It will be appreciated, however, that single chain antibodies (SCAs, such as disclosed in U.S. Pat. No. 4,946,778) and like substances have been developed and may similarly prove efficacious. Biochemistry and genetic engineering may yet produce substances which mimic the function of antibodies in selectively concentrating at the sites of neoplastic tissue (perhaps, even hormones, peptides and other proteins, or the like), though such substances may not be subsumed within the traditional definition of "antibody". "Locator" was chosen as the term to include present-day antibodies and equivalents thereof, as well as those substances yet to be determined which mimic antibodies in the inventive method disclosed herein.

Presently, antibodies useful in the present invention include anti-TAG antibodies, such as for example, B72.3 (an anti-TAG 72 antibody, Dr. Jeffrey Schlom, National Cancer Institute), CC49 (a second generation B72.3 antibody, see U.S. Pat. No. 5,512,443, Arnold, et al., "Intraoperative Detection of Colorectal Cancer with Radioimmunoguided Surgery™ (RIGS®) and CC49 a Second-Generation Monoclonal Antibody (MAb)" *Ann. Surg.*, accepted for publication, *Cancer Res.* 50, 6987–6994, Nov. 1, 1990; *Cancer Res.* 48, 4597–4603, Aug. 15, 1987; *J. Clin. Lab. Analysis* 3: 369–369 (1989); *Biol. Chem,* Hoppe-Seyler, 1989, 370:21–26; *Cancer Res.* 50: 4885–4890, Aug. 15, 1990; *Cancer Res.,* 48: 4588–4596, 1988; *Cancer Res.,* 50: 4872–4879, Aug. 15, 1990; *Cancer* 67: 2880–2886, 1991; *Cancer Res.* 50: 1291–1298, 1990; *Biotechnology,* 3: 378–384, 1985; *Proc. Nat'l Acad. Sci. USA,* 78: 3199–3203, 1981; *Cancer Res.,* 48: 6811–6818, 1988; *Cancer Res.,* 48: 2214–2220, 1988; *J. Nat'l Canc. Inst.* 1986:6666): 995–1003; *Int'l J. Cancer* 1982: 29: 539–545; *Int'l J. Cancer* 1983: 31: 543–551; *Cancer Res.,* 50: 6987–6994, 1990; *Cancer Res.,* 51: 2889–2896, 1991; *J. Clin. Lab. Anal.,* 4: 465–473, 1990; *Cancer Res.,* 51, 6363–6371, Dec. 1, 1991; *J. Nat'l CancerInst.* 82: 1191–1197, 1990; *Cancer Res.* 51, 5378–5383, Oct. 1, 1991); CC83, another second generation B72.3 anti-TAG antibody; CEA antibodies such as $A_5B_7$ monoclonal antibody (Cancer Research Campaign Technology, Ltd, London, England) (see *Int. J. Cancer,* 47: 597–602, 1991; *Br. J. Cancer,* 54:75–82, 1986; *Br. J. Cancer,* 61: 891–894, 1990; *Int. J. Cancer, Supplement* 3, 34–37, 1988; *Eur. J. Nucl. Med,* 13: 197–202, 1987; *Br. J. Cancer,* 60: 549–554, 1989; and *Br. J. Cancer,* 61: 659–662, 1990); monoclonal antibody B17-1A and its $F(ab')_2$ fragment (Wistar Institute, Philadelphia, Pa.); and monoclonal antibody 19–9 and its $F(ab')_2$ fragment (Centocor, Inc., Philadelphia, Pa.).

With respect to the radiolabel of choice, the ability to use a radiation detection probe that can be placed in immediate adjacency to the lymph node means that lower level energy isotopes are preferred, especially those exhibiting photon emissions of energy levels less than about 550 kev, advantageously less than about 300 kev, and preferably less than about 150 kev. $^{125}$I currently is the isotope of choice, though additional low energy isotopes as disclosed in the '840 patent may be used as is necessary, desirable, or convenient. Higher energy level radioisotopes (e.g., $^{131}$I) also may be used, though suitable collimation of the radiation detection probe must be employed which may impede the instrument being facile to the surgeon and limit the areas within the body cavity which can be suitably surveyed.

In addition to radioisotopes emitting gamma radiation, radioisotopes exhibiting beta radiation additionally can be used in conjunction with a probe which can detect beta radiation or positrons. The detection of beta radiation intra-operatively is disclosed, for example, in U.S. Pat. No. 5,008,546, the disclosure of which is expressly incorporated herein by reference.

The dosage of labeled locator is such that the radiation detection probe can be utilized for determining lymph node sites exhibiting accretion of the radiolabeled locator. Such dosages depend upon the specific type of label, the type of locator, and like factors which may affect dosage requirements as those skilled in the art will appreciate.

With respect to the detection of lymph node sites exhibiting accretion of the radiolabeled locator, reference is made to the following patents which show a preferred hand-held probe for the detection of gamma radiation: U.S. Pat. Nos. 4,801,803, 4,889,991, and 5,070,878, the disclosures of which are expressly incorporated herein by reference. As stated above, U.S. Pat. No. 5,008,546 discloses a probe suitable for the detection of beta radiation. Additional radiation detection devices can be used as is necessary, desirable, or convenient. In this regard, it will be appreciated that intraoperative accessing of the patient in order to determine lymph node involvement is but one alternative for practice of the present invention. Additionally, probes may be used as part of an laproscope, mediastinoscope, or like specific instrument which suitably can be outfitted with a miniaturized radiation detection device which can be placed in immediate adjacency with the lymph node in order to determine accretion of radioactivity. Regardless of the instrument or technique employed, the present invention encompasses all such instruments and techniques, by whatever label.

As is reported in the '840 patent, the immediate accession of the patient with the radiation detection probe is not advisable. Preferably, time is permitted to elapse following administration of the radiolabeled locator in order for unbound radiolabeled locator to be cleared from the tissue surrounding the lymph nodes to be surveyed. Suitable radiation detection probes function by determining a level of radioactivity over and above that normal background radioactivity found at the location (e.g., operating room) where the patient is being surveyed as well as the blood pool background (radiolabeled locator circulating in the blood stream), and surrounding tissue which may contain circulating unbound radiolabeled locator. The time may be as short as a few minutes on up to several weeks, depending upon how fast the patient's body clears (often metabolizes) the radiolabeled locator. Of importance is the recognition that the radiolabeled locator will be bound to the tumor cell site with its radiolabel intact, albeit at reduced levels, after such time period has elapsed. Importantly, it is inappropriate to survey the lymph nodes based upon maximum tumor uptake of the radiolabeled locator as is traditionally taught in external scintigraphy and external imaging technology.

Once the suitable interval has elapsed, the patient is accessed with the radiation detection probe and lymph node sites are surveyed with the probe for determining accretion of radiolabeled locator by detecting with the probe elevated levels of radiation at the lymph node sites. Besides the determination of micrometastatic tissue which may alter the course of surgical treatment as disclosed in the '840 patent, the present invention now enables the physician to determine lymph nodes which are enriched in CD4+ lymphocytes for use in preparing a therapeutic agent for the regression of neoplastic tissue (cancer).

The determined lymphocyte cells then are expanded or proliferated in a manner that importantly departs from conventional cell expansion in prior immunotherapy procedures. Briefly, cell expansion involves the steps of dissociation of LNL from lymph node tissue; ex vivo activation and initiation of cell expansion; media changes, cell culture splitting, and weaning from exogenous cytokines; and cell harvest and preparation of final product for administration to the patient.

Cell and tissue dissociation is accomplished conventionally, such as by centrifugation, in order to harvest the LNLs. Initiation of cell expansion includes the initial use of serum-free Macrophage SFM media which is unique to this cell expansion regimen. Additionally, mitogenic stimulation most preferably is conducted using IL-2 and soluble anti-CD3 cells which are simultaneously added (rather than sequential addition and the use of plate-bound anti-CD3 cells, as in the art). Aliquots of fresh media and cytokine are periodically added to the culture during their growth. Importantly, the cells are weaning from exogenous cytokines (e.g., IL-2) by incorporating only fresh media so as to lower the amount of IL-2, say, to less than 20 Cetus units/mL of culture.

Administration of the supernatant from the expanded lymphocytes or the expanded lymphocytes themselves to the patient is accomplished as taught in application Ser. No. 08/271,902 now U.S. Pat. No. 5,814,295. Thereafter, the patient is administered the chemotherapeutic prescribed by the physician. Alternatively, the supernatant can be simultaneously administered to the patient along with the chemotherapeutic of choice. It also is possible to administer the expanded lymphocytes to the patient along with the supernatant therefrom as taught in application Ser. No. 08/271, 902 now U.S. Pat. Not. 5,814,295 because the lymphocyte cells secrete the material that forms the supernatant. The following examples will show how the present invention has been practiced, but it should not be construed as limiting. All references cited herein are expressly incorporated herein by reference.

EXAMPLES

PRE-CLINICAL DATA

Materials and Methods

Cell Lines

Human colorectal carcinoma cell lines LS174R, LS513, and SW480 were obtained from the American Type Culture Collection (Rockville, Md.). The CAV cell line was developed at The Ohio State University James Cancer Hospital and Research Institute from a liver metastasis of a patient with colon adenocarcinoma. Cells were cultured at 37° C. in 5% $CO_2$ in their maintenance media, which media consisted of RPMI-1640 with 2 mM glutamine and 10% fetal bovine serum (FBS; Gibco BRL, Grand Island, N.Y.).

Chemotherapeutics

The following chemotherapeutics were evaluated:

5-FU—Pharmacia and Upjohn Company, Kalamazoo, Mich.

Doxorubicin HCL—Gensia Laboratories Ltd., Irvine, Calif.

Etoposide phosphate—Bristol Myers Squib Company, Princeton, N.J.

Irinotecan HCl—Pharmacia and Upjohn Company, Kalamazoo, Mich.

Gemcitabine HCl—Eli Lilly and Company, Indianapolis, Ind.

Lymphocyte Culture and Supernatants

Lymphocytes were separated from lymph nodes localized and obtained at laparotomy using the radiolabeled monoclonal antibody, CC49, as described in application Ser. No. 08/271,902 now U.S. Pat. No. 5,814,295. Lymph node cells were suspended at $10^6$/ml in expansion media which consisted of modified AIM-V (Macrophage-SFM, Gibco BRL) with 10 µg/ml gentamicin to which 100 U/ml of human recombinant interleukin-2 (IL-2, Proleukin brand, Cetus Oncology Corporation, Emeryville, Calif.) and 10 ng/ml anti-CD3 monoclonal antibody (OKT3 brand, Ortho Biotech, Raritan, N.J.) were added. Cells were cultured at 37° C. for 4 days and then were resuspended at $0.25 \times 10^6$/ml in expansion media containing 20 U/ml IL-2 for 3 days and at $0.5 \times 10^6$/ml in expansion media containing 20 U/ml IL-2 for 3 more days.

Two different formulations of soluble products of the expanded cells were evaluated:

"Unstimulated" supernatant consisted of the supernatant collected at day 10 of lymphocyte expansion after centrifugation at 200 g.

"Stimulated" supernatant consisted of supernatants collected after the day 10 lymphocytes had been recultured in vitro at $10^6$/ml in expansion media for an additional 24 hours in T75 plastic flasks (Becton Dickinson Labware, Franklin Lakes, N.J.) in which OKT3 had been previously immobilized by culturing in Hank's Balanced Salt Solution for 18 hours.

Both freshly collected supernatants and supernatants that had been frozen at -20° C. and then thaws were evaluated.

Proliferation Assay

Unstimulated and Stimulated supernatants, as well as the expansion media, were added at a range of volumes to colorectal cancer cells cultured in their maintenance media in 24-well plates for 96 hours. MTS was added for the final 5 hours of culture as recommended by the manufacturer (CelTiter 96 Aq$_{ueous}$ Non-Radioactive Cell Proliferation Assay, Promega, Madison, Wis.), and the absorbence was read in a DigiScan reader (ASYS Hitech, Austria) at $A_{492}$ nm. Samples were evaluated in triplicate. Colorectal cancer cells cultured in maintenance media alone were used as controls. Fractional inhibition was determined by the following formula:

(Experimental Absorbence—Absorbence of Maintenance Media Alone) (Absorbence of Cells in Maintenance Media With No Additions—Absorbence of Maintenance Media Alone)

Cell Cycle Analysis

Analysis of cell cycle was performed using propidium iodide (PI) on a Coulter EPICS Elite flow cytometer (Coulter Corporation, Miami, Fla.) equipped with a 488 nm, 15 mW, air-cooled Argon laser (see Darzynkiewicz, et al., *Methods in Cell Biology: Flow Cytometry*, 2nd Edition, Part A, 1995, pp. 32–36). Optical lased alignment calibration of the flow cytometer was performed using Coulter's DNA-Check EPICS alignment fluorosphere beads with coefficient of variations routinely less than 2%. PI fluorescent light emission was collected through a 610 nm, long-pass transmission filter. PI signal was measured in linear mode and extended analysis of DNA content was performed using the ModFit LT program (Verity Software House, Inc., Topsham, Me). Data are presented as the percentage of cells in F1–G0, S, and G2–M.

Cytokine Levels

Commercially available enzyme-linked immunoabsorbent assay (ELISA) kits were used to quantify IL-1a, IL-4, interferon (IFN) g, tumor necrosis factor (TNF) a, and granulocyte-macrophage colony stimulating factor (GM-CSF) (R&D Systems Inc., Minneapolis, Minn.). Assays were conducted in duplicate according to the recommendations of the manufacturers.

Reverse Transcription (RT) Polymerase Chain Reaction (PCR)

Thymidylate synthetase and mdrl mRNA levels were assessed using RT-PCT. Total RNA was extracted from cultured tumor cells using TRIzol (Gibco/BRL, Gaithersburg, Md.) according to the manufacturer's instructions. 1 µg of total RNA was converted to double stranded cDNA using superscript II Reverse Transcriptase (Gibco/BRL) according to the manufacturer's instructions. The RT reaction (2 µl) was amplified in a PCT consisting of: 1.6 µl of 10 PCR Buffer (500 mM KCl, 200 mM Tris HCl, pH 8.3), 0.4 µl of 50 mM MgCl$_2$, 0.5 U of Taq DNA Polymerase, and 1 µl of the relevant 10 µM oligonucleotide primer set in a 20 µl reaction. The primer set for mdrl consisted of 5'-ATCGTGAGGGCAGCAAAGGA (SEQ ID No.:1) and 3'-GTGGACAGGCGGTGAGCA (SEQ ID NO.:2) (product=275 bp). The primer set for thymidylate synthetase consisted of 5"-CCCTCTGCTGACAACCAA (SEQ ID NO.:3) and 3'-CCCCAAAATGCCTCCACTGG (SEQ ID NO.:4) (product=218 bp). These primer sequences were obtained by using Oligo Primer Analysis Software, Version 5.0 (National Biosciences, Inc. (Plymouth, MN) which analyses gene sequences from a genebank and derives sets of unique primers for use in the PCR assays. The gene sequences selected are available to the public at http://www2.ncbi.nlm.nih.gov/genebank. PCR reactions were performed with a Hybaid thermocycler for 27 cycles of template denaturation (94° C. for 20 seconds), primer annealing (60° C. for 30 seconds), and extension (72° C. for 1 minute). GAPDH cDNA was amplified for 22 cycles to serve as both a positive amplification control and to serve as a template equality control. Amplified PCR products were separated in a 2% agarose gel and visualized on an UV illuminator. Experiments and RT-PCR were repeated thrice.

P-Glycoprotein

Accumulation of Doxorubicin, a fluorescent anthracycline, was measured as a function index of P-glycoprotein activity. For these studies, cells were cultured in phenol red-free RPMI-1640, supplemented with 10% FBS. They were trypsinized and washed with phenol d-free RPMI-1640/5% FBS, aliquoted and incubated for an hour at 37° C. in phenol red-free RPMI-1640/5% FBS containing 2 µM Doxorubicin. After incubation, cells were washed twice with medium and held on ice. Fluorescence intensity of $1 \times 10^4$ cells then was determined by flow cytometry for each treatment group. P-glycoprotein also was evaluated using monoclonal antibody, MRK16 (Kaumiya Biomedical Company, Thousand Oaks, Calif.), which recognizes an external epitope. Cells incubated with mouse IgG (Sigma, St. Louis, MO) served as negative controls. A fluorescein-conjugated goat anti-mouse antibody (DAKO Corporation, Carpinteria, Calif.) was used as a secondary antibody. After washing, the fluorescence intensity of 1.5× $10^4$ cells per group was measured with a Coulter EPICS Elite flow cytometer. Data were stored in listmode format, and extended analysis was performed using Coulter Elite software.

Statistical Analysis

The combined effects of the drugs and supernatants were analyzed by the median effect method of Chou and Talalay using CalcuSyn software (Biosoft, Ferguson, Mo). In brief, when two agents are administered at a fixed ratio, a combination index (CI) is calculated depending on whether the drugs are assumed to be mutually non-exclusive or mutually exclusive in their action (see Chou, et al., "Quantitative analysis of dose-effect relationships: the combined effects of multiple drugs or enzyme inhibitors", *Adv Enzyme Regul*, 22:27–55, 1984). According to this method, "synergy" is indicated by a CI of less than 1, "addition" by a CI equal to 1, and "antagonism" by a CI greater than 1. A CI of less than 0.3 is considered to represent "strong synergism", and a CI greater than 3.3 is considered to represent strong antagonism".

RESULTS

Characteristics and Effects of Supernatants

FIG. 1 shows the effect of the Unstimulated supernatants, Stimulated supernatants, and the expansion media supplemented with 20 U/ml IL-2 on the growth of LS174T cells when added at a 25% volume/volume (v/v) to LS174T cells in maintenance media. Both freshly collected supernatants and supernatants that had been frozen at −20° C. and then thawed were evaluated.

Figure 2:
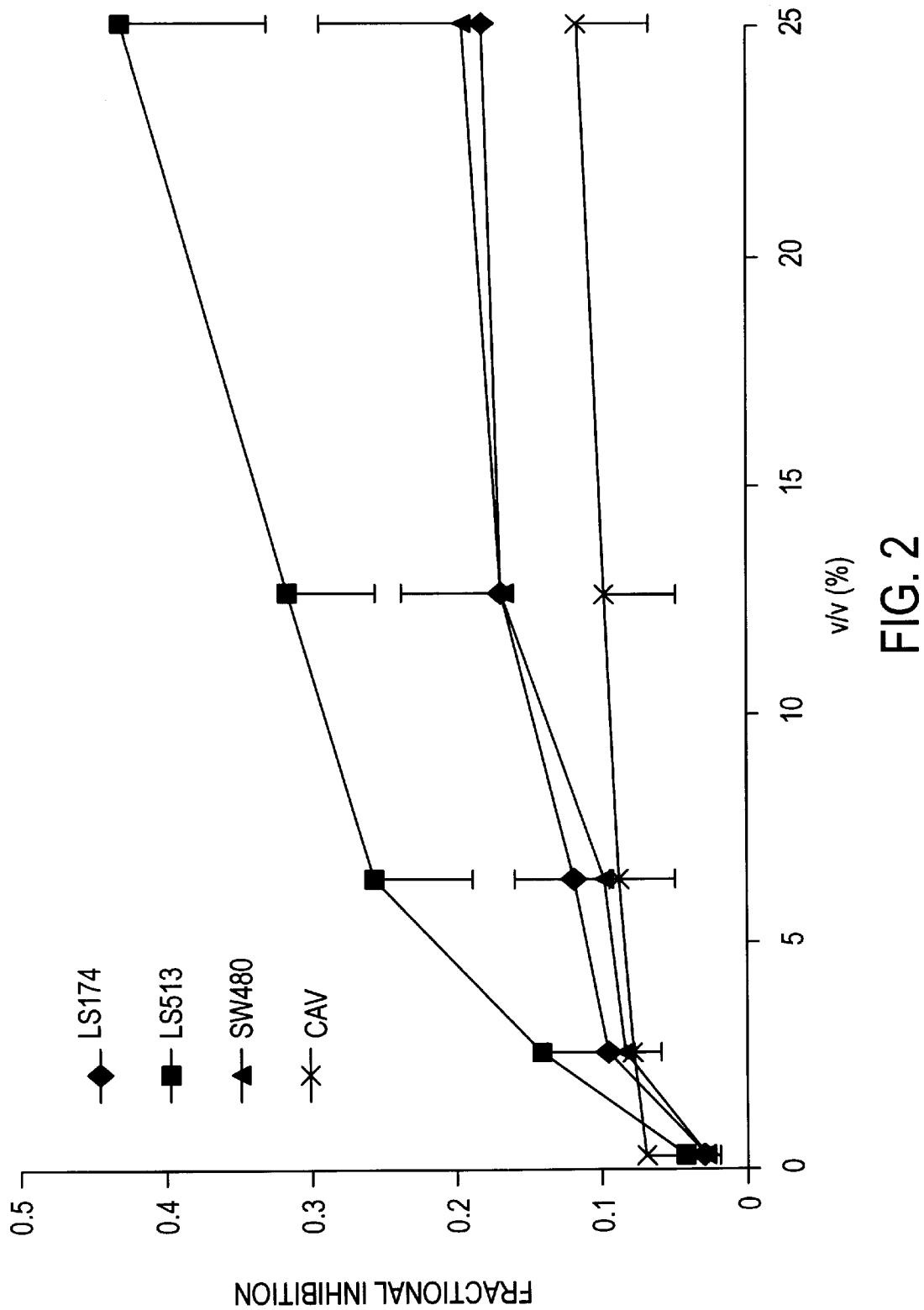
FIG. 2 depicts the effects of Stimulated supernatant on the growth of colorectal cancer cells added at a range of concentrations.

The effects of a range of concentration of the Stimulated supernatants on the growth of LS 174T, which express the TAG-72 epitope in vivo, and other colorectal cancer lines are compared in FIG. 2. These studies demonstrated that factors produced by the expanded lymphocytes had antiproliferative activity. These studies also indicate that sensitivity to these soluble factors varied among the colorectal cell lines tested.

Figure 3:
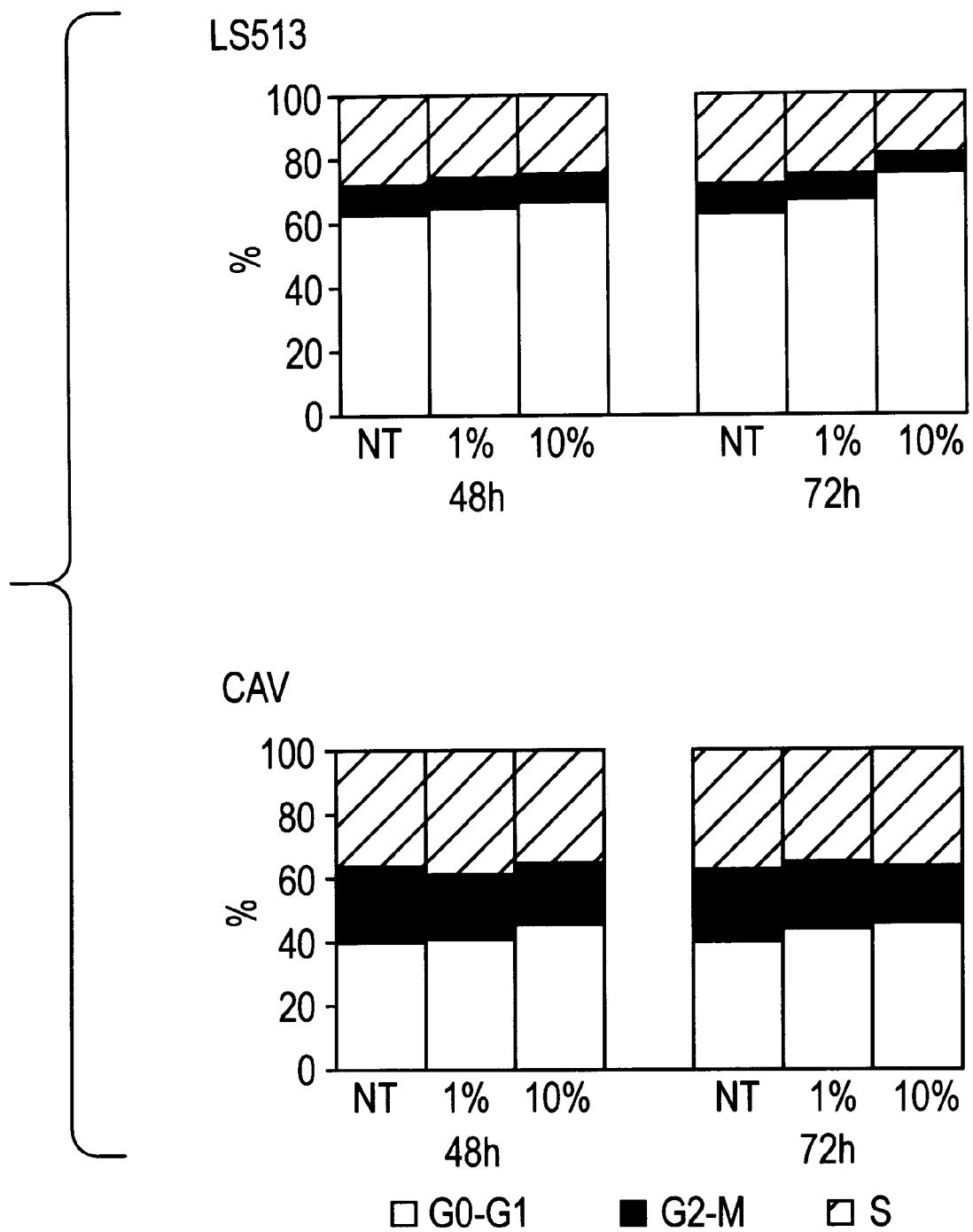
FIG. 3 depicts the effects of Stimulated supernatant added at 1% or 10% (v/v) on the cell cycle of LS513 (top) and CAV (bottom) cells after 48 and 72 hours of culture.

The effects of the stimulated supernatant on cell cycle are displayed in FIG. 3, which indicate that the primary effect is an increase in cells in G0–G1. The expansion regimen yields a mixed population of CD4$^+$ and CD8$^+$ lymphocytes.

Figure 4:
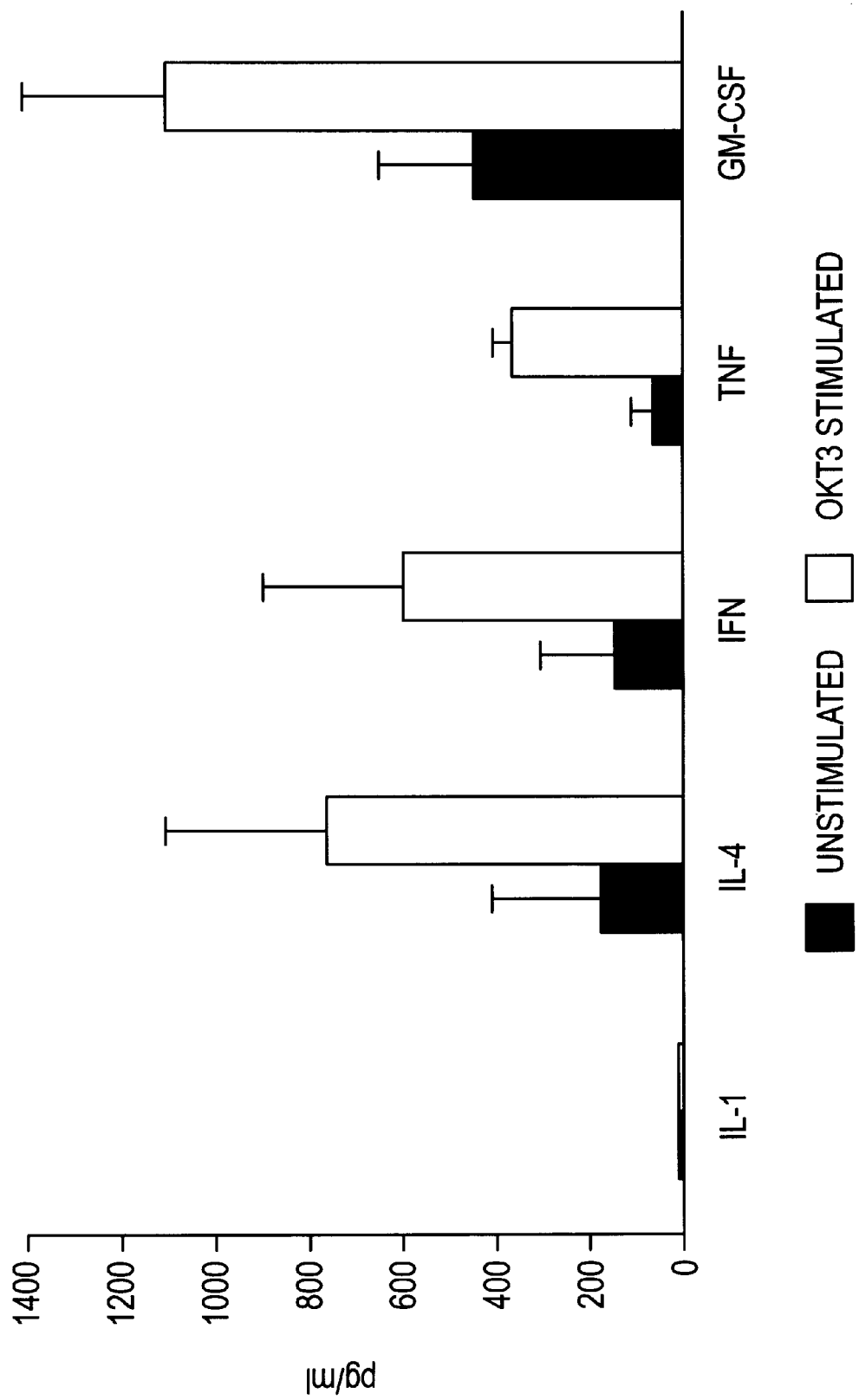
FIG. 4 depicts the cytokine levels of Unstimulated and Stimulated supernatants. Data represent mean ± SD for supernatants from six different lymphocyte expansions.

The levels of various cytokines that are observed in the Unstimulated and Stimulated supernatants are presented in FIG. 4.

Combined Effects of Supernatant and Chemotherapeutics

Figure 5:
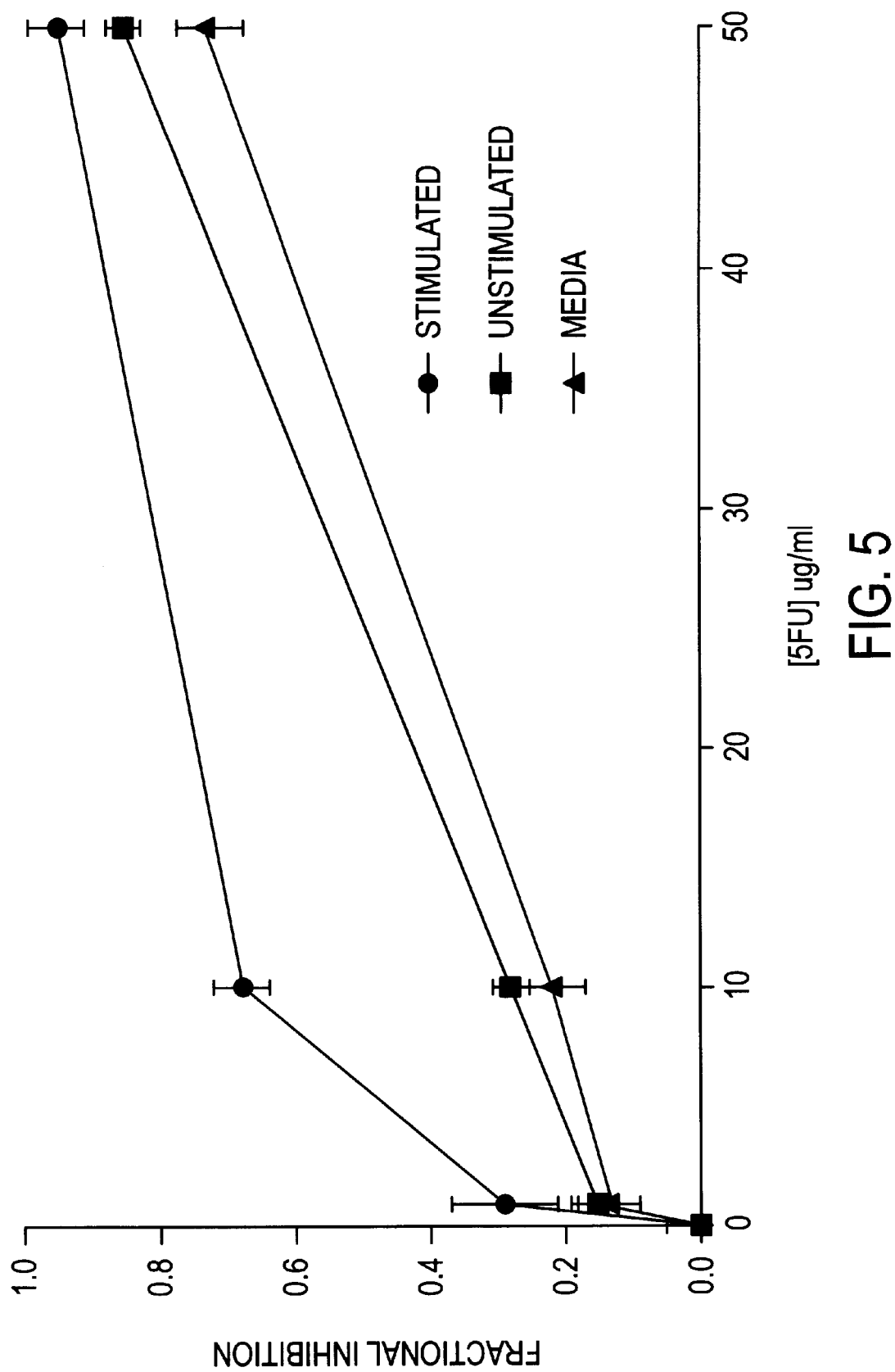
FIG. 5 depicts the effects of Stimulated and Unstimulated supernatants and expansion media supplemented with IL-2 (Media) added at 25% (v/v) on the antiproliferative activity elicited by a range of concentrations of 5-FU. Data represent mean ± SD for three different experiments using LS 174T cells.

The combined effects of 5-FU and supernatants were first tested in LS174T cells cultured with a range of concentrations of 5-FU and a fixed concentration of supernatants or of expansion media supplemented with 20 U/ml of IL-2. These results are displayed graphically in FIG. 5. The addition of supernatants, the Stimulated supernatants in particular, enhanced the antiproliferative effects of 5-FU in LS154T cells; the expansion media supplemented with 20 U/ml of IL-2 did not.

Figure 6:
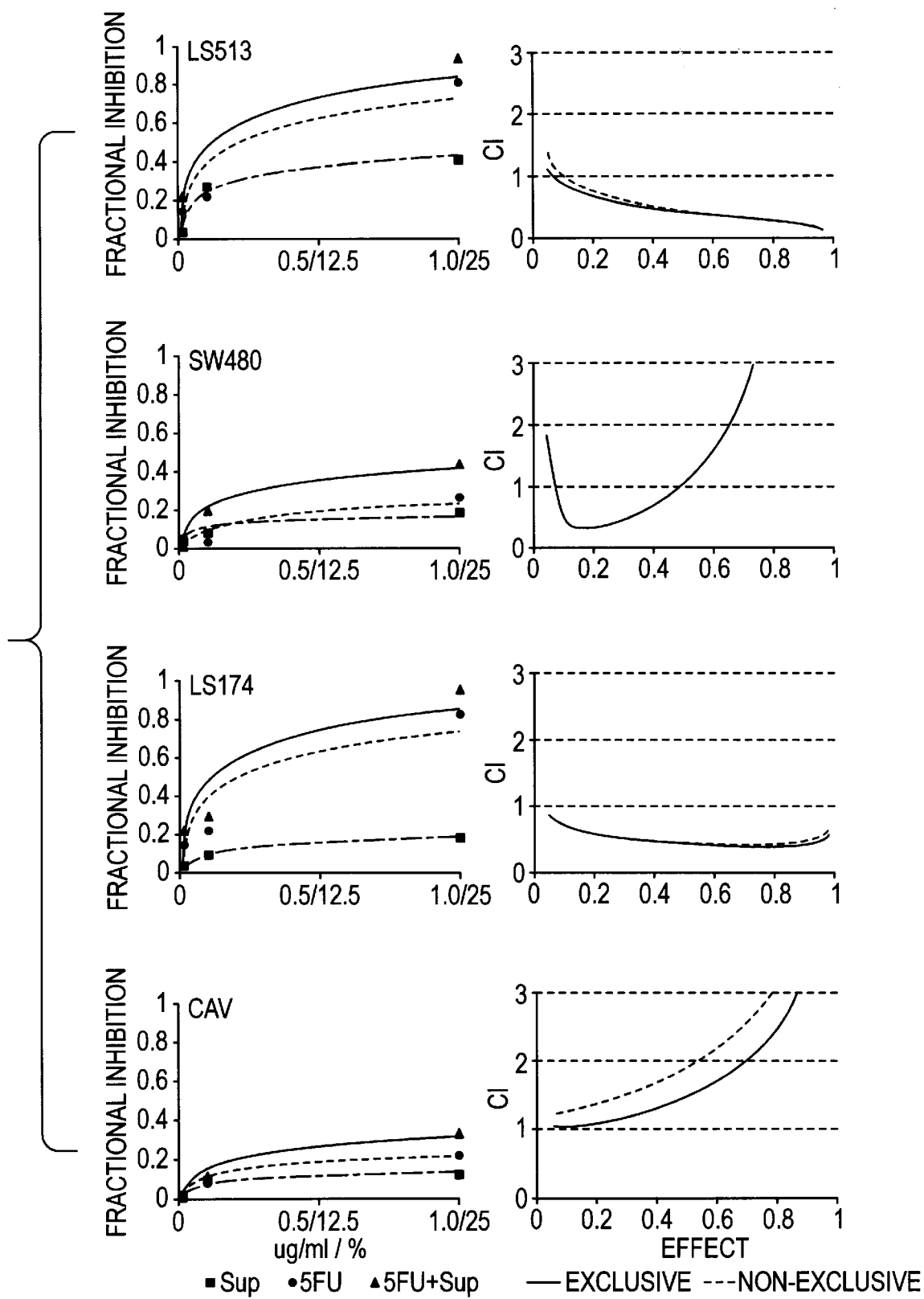
FIG. 6 depicts the combined effects of 5-FU and Stimulated supernatants on colorectal cancer cells. The left column graphically displays the antiproliferative activity and the right column displays the CI plotted with the assumption that the agents are mutually exclusive or mutually non-exclusive in their mechanism of action Data represent the mean of three experiments for CAV and SW480 cells and four experiments for LS513 and LS 174T cells.

Colorectal cancer cells then were cultured at a constant ratio of Stimulated supernatant and 5-FU to analyze the combined effects. These results are displayed graphically in FIG. 6. The interactions varied with the agent and the cell line. Synergistic antiproliferative interactions with CI less than 1.0 were demonstrated with 5-FU and supernatants in LS174T and LS513 cells. In SW480 cells, synergistic antiproliferative activity was observed primarily at low growth inhibition. 5-FU- supernatant antagonism was demonstrated in CAV cells, which also express the TAG-72 epitope in vivo.

Figure 7:
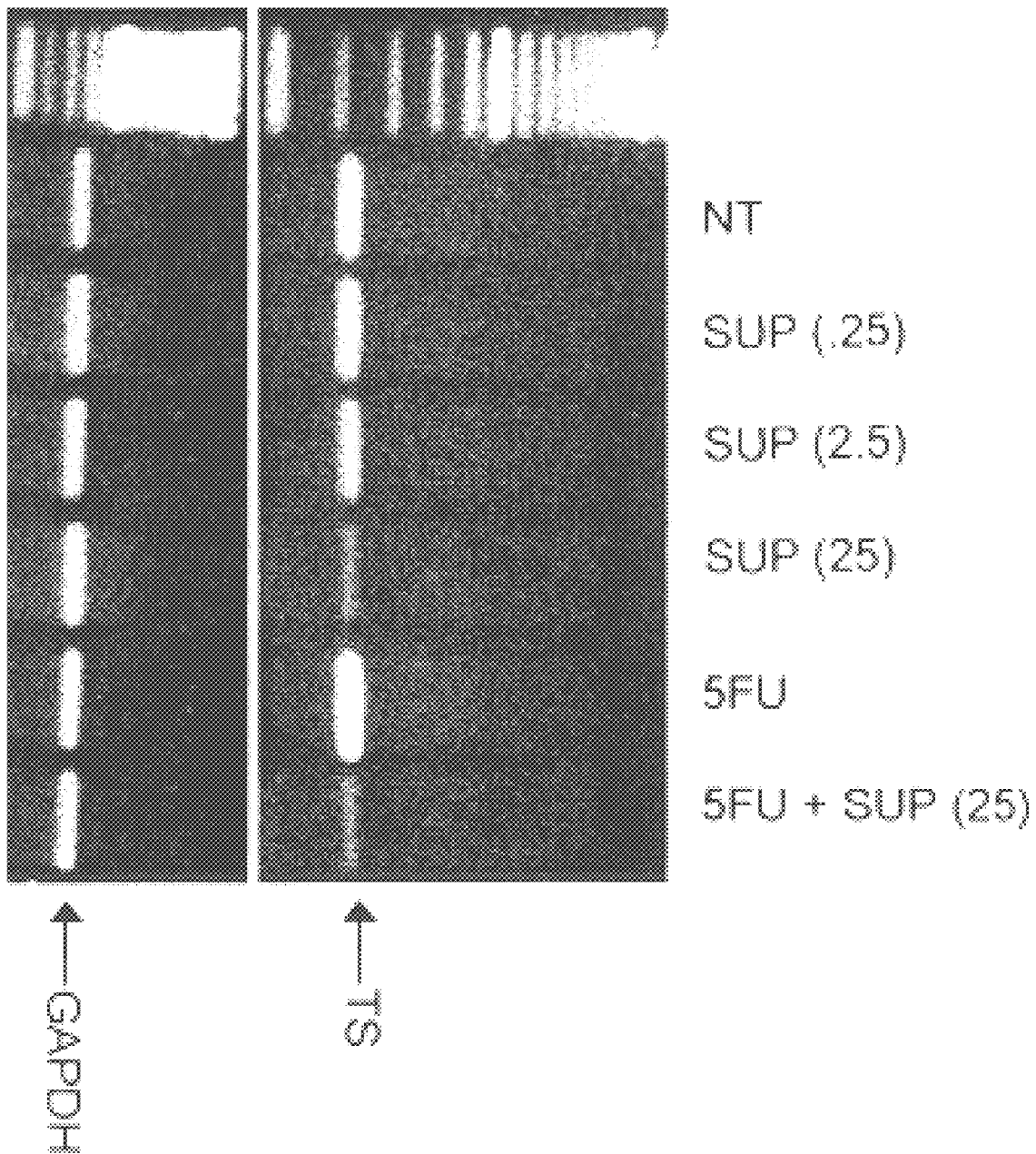
FIG. 7 depicts the effects of Stimulated supernatants added at 0.25%, 2.5%, and 25% (v/v); 5-FU (10 μg/ml); or 5-FU (10 μg/ml) plus supernatant (25%) on thymidylate synthetase (TS) mRNA expression of LS513 cells. Cells were cultured for 48 hours.

A potential mechanism of interaction between 5-FU and the supernatant is at the level of thymidylate synthetase, the target of 5-FU. This possibility was examined by assessing thymidylate synthetase mRNA expression. In LS513 cells there was a slight decrease in thymidylate synthetase mRNA expression with exposure to the stimulated supernatant, both in the presence and absence of 5-FU. These results are displayed graphically in FIG. 7. Similar alterations in thymidylate synthetase mRNA was not observed in LS 174R and SW480 cells.

Figure 8:
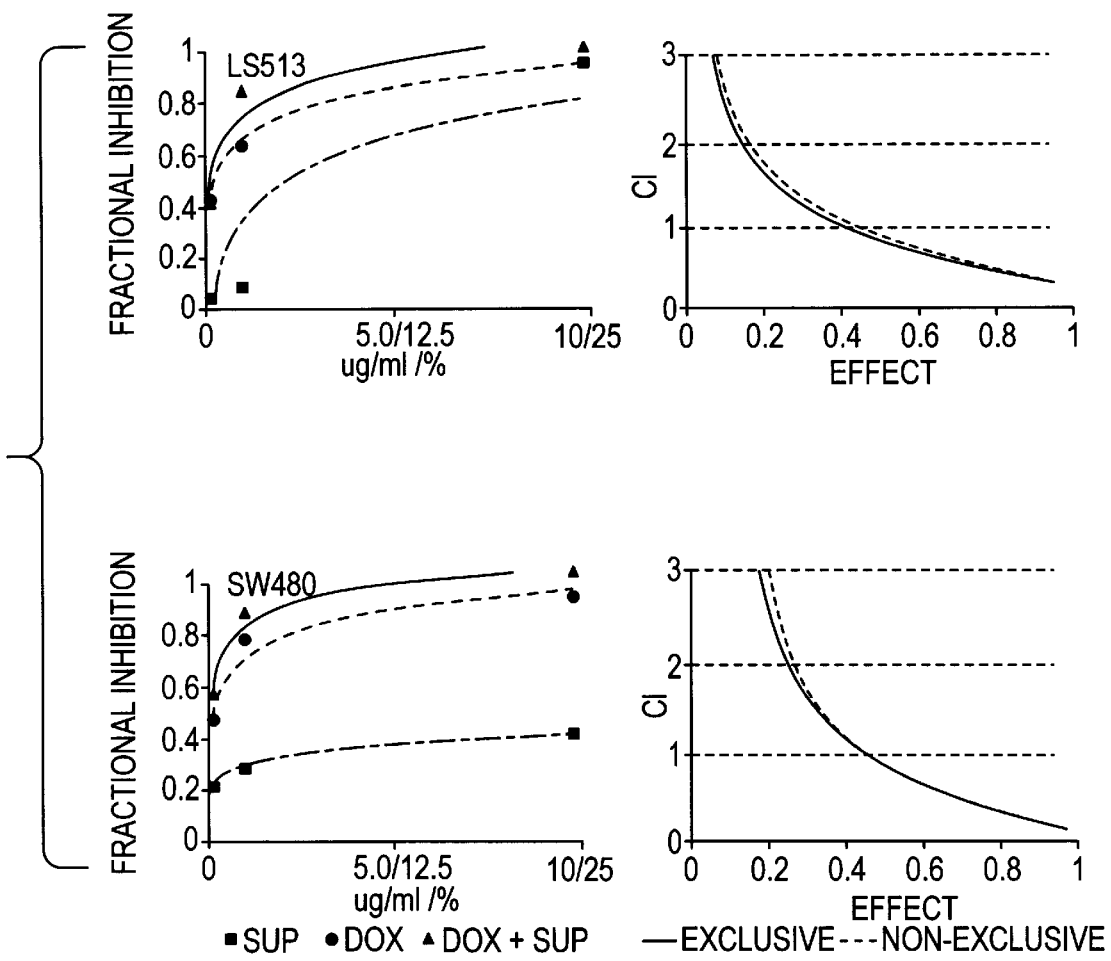
FIG. 8 depicts the combined effects of Doxorubicin (Dox) and Stimulated supernatants on colorectal cancer cells. The left column displays the antiproliferative activity and the right column displays the CI plotted with the assumption that the agents are mutually non-exclusive or are mutually exclusive in their mechanism of action. Data represent the mean of three experiments.
Figure 9:
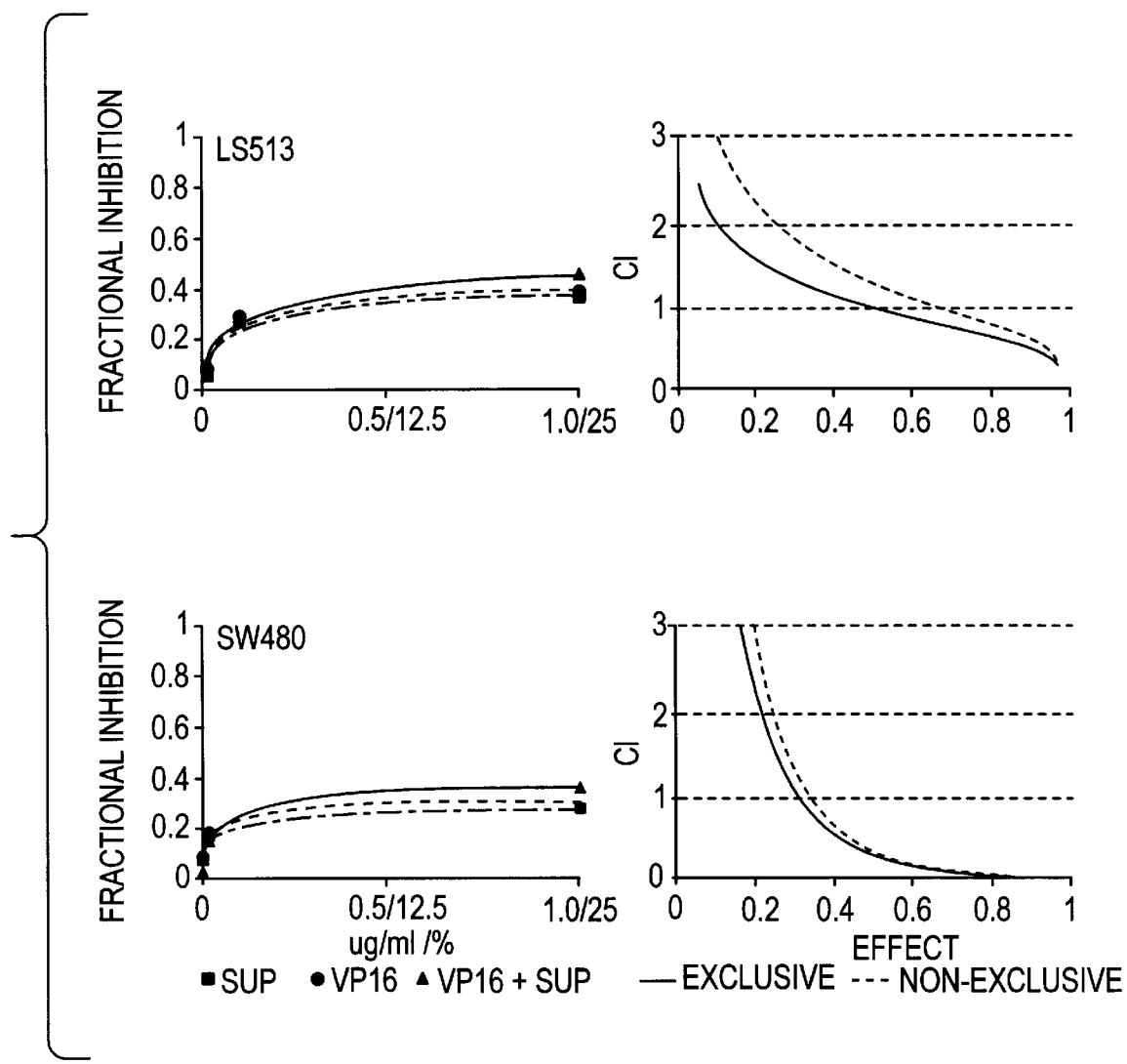
FIG. 9 depicts the combined effects of Etoposide (VP16) and Stimulated supernatants on colorectal cancer cells. The left column displays the antiproliferative activity and the right column displays the CI plotted with the assumption that the agents are mutually non-exclusive or are mutually exclusive in their mechanism of action. Data represent the mean of three experiments.
Figure 10:
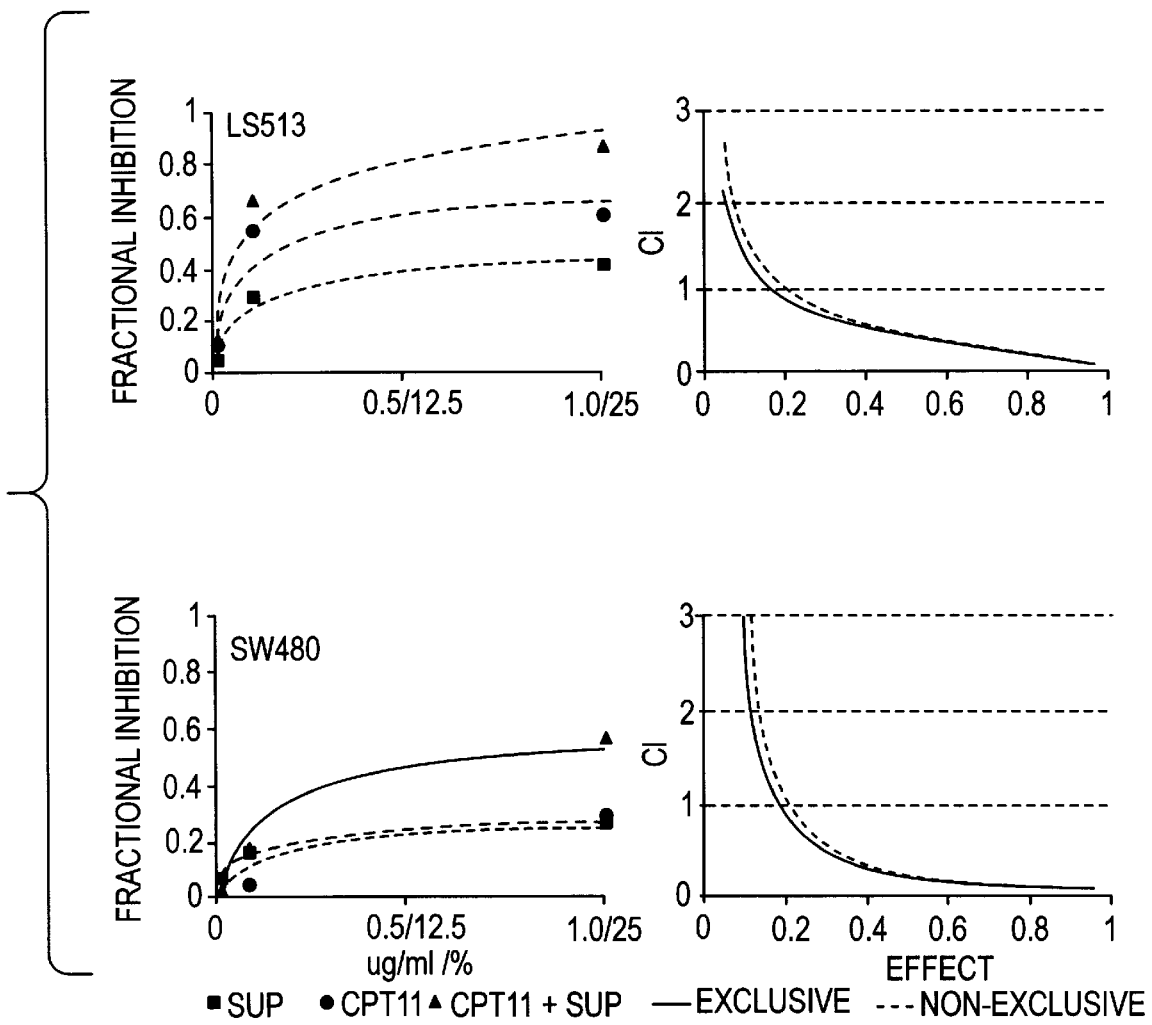
FIG. 10 depicts the combined effects of Irinotecan (CPY11) and Stimulated supernatants on colorectal cancer cells. The left column displays the antiproliferative activity and the right column displays the CI plotted with the assumption that the agents are mutually non-exclusive or are mutually exclusive in their mechanism of action. Data represent the mean of four experiments.
Figure 11:
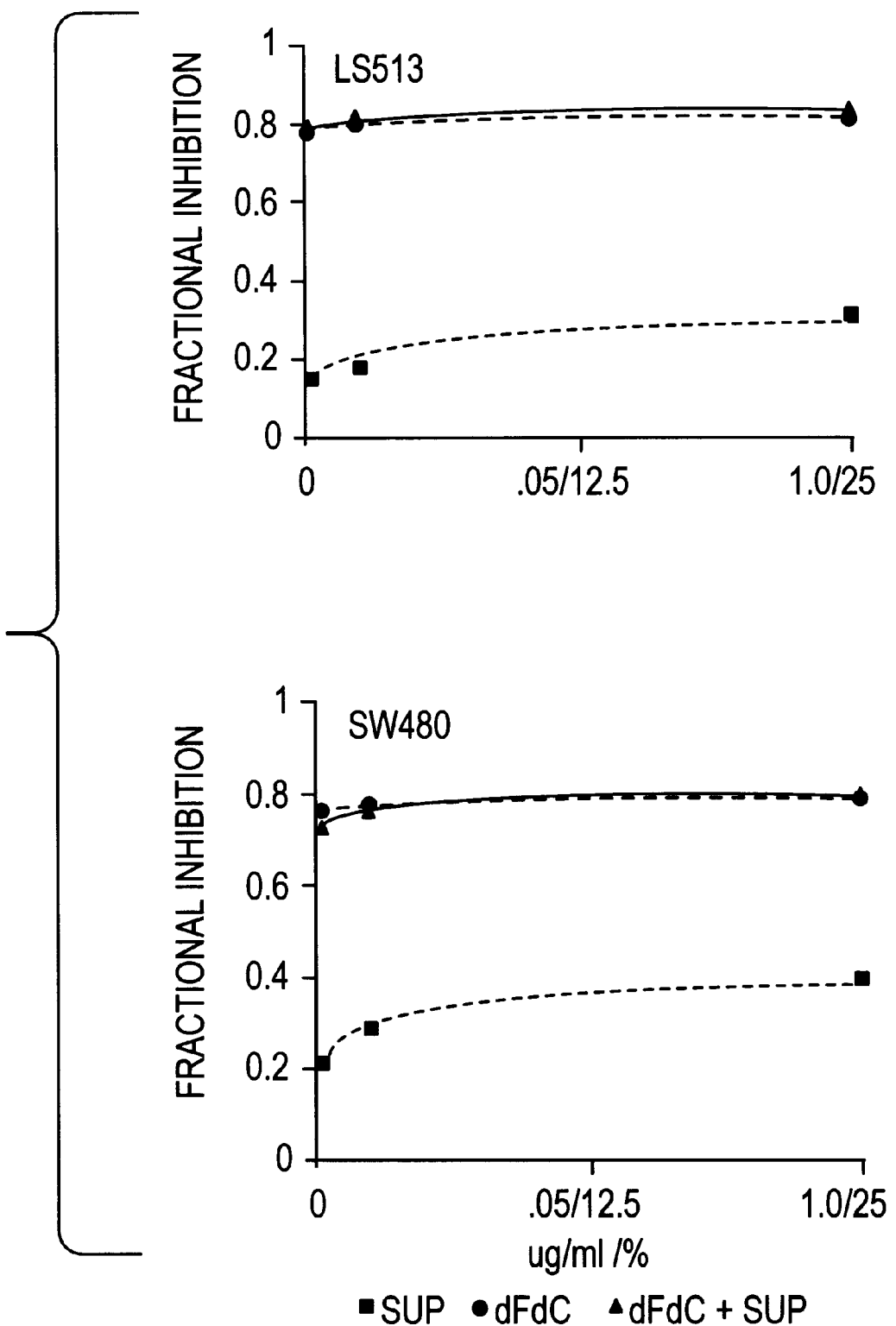
FIG. 11 depicts the combined effects of Gemcitibine (dFdC) and Stimulated supernatants on colorectal cancer cells. Data represent the mean of two experiments.
Figure 12:
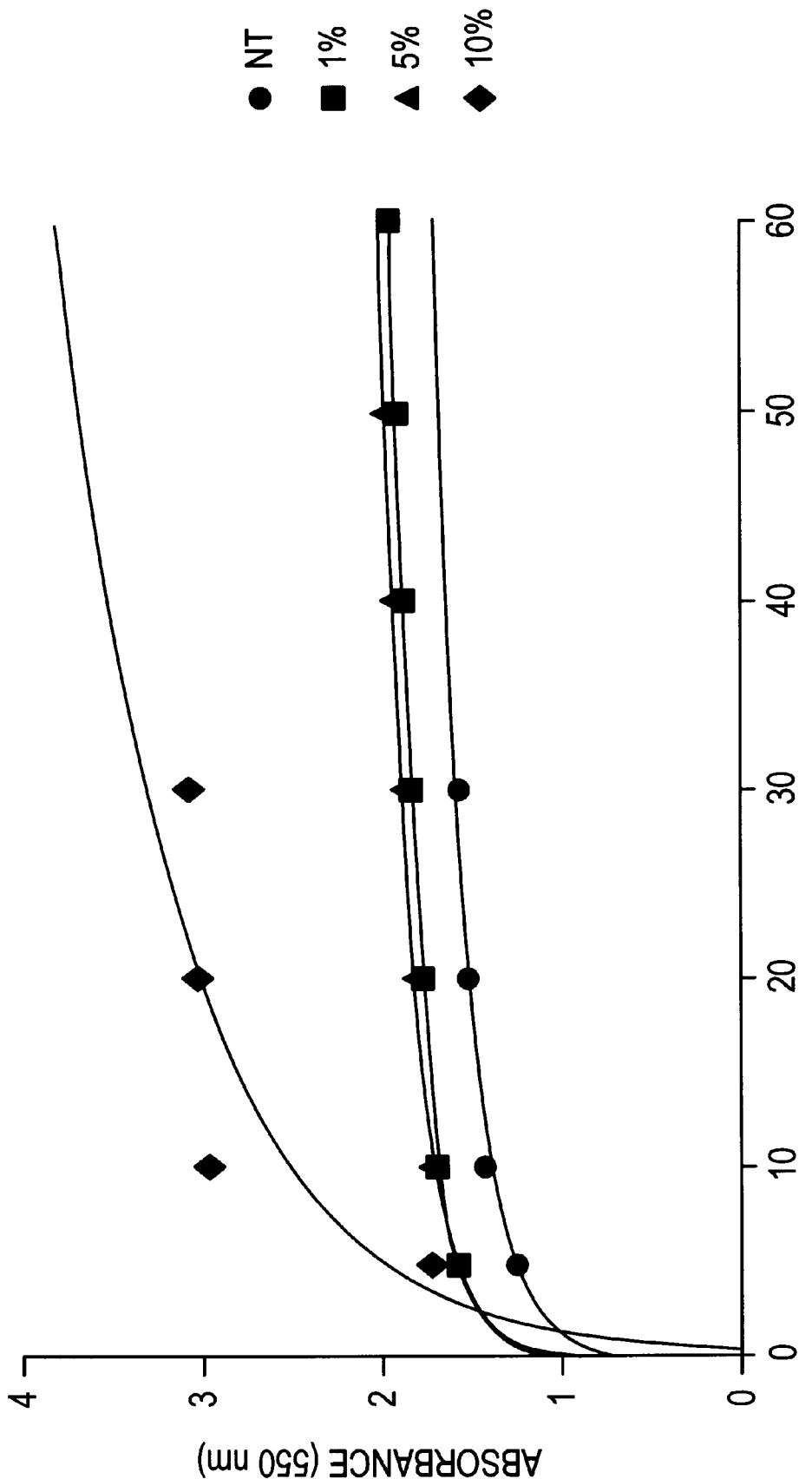
FIG. 12 depicts the effect of Stimulated supernatant added at 1.0%, 5.0%, or 10% (v/v) on Doxorubicin uptake by LS513 cells. NT=Doxorubicin uptake in the absence of supernatant.

Colorectal cancer cells were cultured at a constant ratio of Stimulated supernatant and Doxorubicin (FIG. 8), Etoposide (FIG. 9), Irinotecan (FIG. 10), and Gemcitibine (FIG. 11). Synergistic interactions were observed at high levels of antiproliferative activity with Doxorubicin, Etoposide, and Camptosar in LS513 cells. Antagonism with CI greater than 10 was observed with Gemcitabine. A potential mechanism of interaction with Doxorubicin is the modulation of multidrug resistance and the expression of P-glycoprotein; SW480 also do, but to a lesser extent. As a functional measure of P-glycoprotein, Doxorubicin uptake was assessed by flow cytometry. The addition of supernatant did enhance Doxorubicin uptake (FIG. 12).

Figure 13:
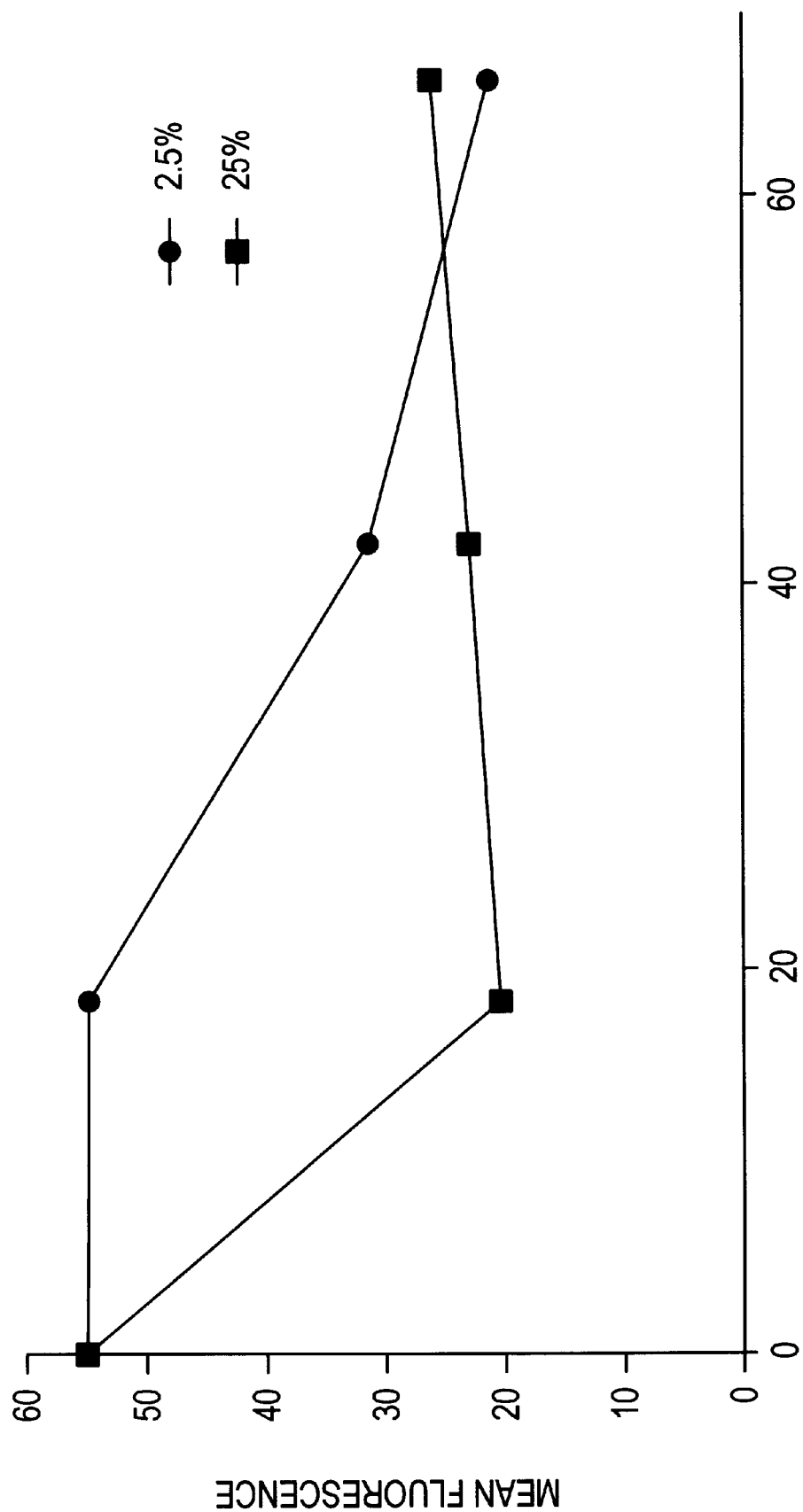
FIG. 13 depicts the effect of supernatant on P-glycoprotein expression by LS513 cells.

The effects of the stimulated supernatants on P-glycoprotein expression as detenmined by monoclonal antibody and flow cytometry are displayed in FIG. 13. The expression of mdrl gene using PCR also was performed; consistent changes were not detected.

CLINICAL DATA

Patients that were treated as reported in co-pending application serial number 08/271,902 now U.S. Pat. No. 5,814,295, cited above, and additional patients in the same study, were evaluated for their response to 5-FU pre- and post-treatment in accordance with the therapeutic agents disclosed in co-pending application serial number 08/271,902 now U.S. Pat. No. 5,814,295. For purposes of determining an objective response to the chemotherapy, only a complete or a partial response would be considered, where a "partial response" means a >50% reduction in the sum of the products of the bi-dimensional measurements for at least 4 weeks and no new lesions. The "onset of response" is defined as the date of assessment at which the 50% reduction was first noted. The definition of "refractory" used here was that (1) the patient either progressed on 5-FU while receiving adjuvant treatment, or (2) the patient progressed while on 5-FU for the treatment of metastatic disease.

The following table summarizes these anecdotal findings:

TABLE 1

| Pa-tient No. | Pre-Therapy | | Post-Therapy | | |
|---|---|---|---|---|---|
| | 5-FU Regimen | Best Response | 5-FU Regimen | Time to 5-FU From Therapy | Best Response |
| 3 | 5-FU/ Leuc/Leva (adj) | Stable at best (5 mos.) | Intrahepatic 5-FU, Mitomy. | 7 mos. | PD |
| 6 | 5-FU (adjuvant) | Stable (8.5 mos) | 5-FU/Leuc/ interf. | 4 mos. | Stable (15 mos.) |

TABLE 1-continued

| Pa-tient No. | Pre-Therapy | | Post-Therapy | | |
|---|---|---|---|---|---|
| | 5-FU Regimen | Best Response | 5-FU Regimen | Time to 5-FU From Therapy | Best Response |
| 14 | 5-FU (adjuvant) | Stable (unknown) | 5-FU/Leuc/ mitomycin | 10 mos. | Stable at best (9 mos.) |
| 16 | 5-FU/ Leuc/ interf. (palliative) | PR | 5-FU | 16 mos. | Almost PR (not 50%) |
| 31 | 5-FU/Leuc | PD | 5-FU | 5 mos. | Stable at best (3–4mos.) |
| 32 | 5-FU/leuc/ leuc misole (adj) | PD | 5-FU/leuc | 4 mos. | Stable at best (4 mos.) |
| 37 | 5-FU/leuc (adj) | PD | 5-FU/ intra-arterial FUDR | 5 mos. | PR (9 mos.) | interf = interferon α
leuc = leucovorin
mitomy = mitomycin
FUDR = floxuridine
adj or adjuvant = adjuvant chemotherapy These results demonstrate that patient 37 had a response on 5-FU following therapy after having progressive disease on the combination of 5-FU and leucovorin. She was treated with four cycles of 5-FU and leucovorin in an adjuvant setting and progressed within 2 months. She began 5-FU as a continuous infusion and FUDR intra-arterially approximately 5 months after therapy. At that time, she had multiple liver lesions. From her scans about 3 and 4 months later, it appeared that she met the criteria for a partial response. Unfortunately, there are no subsequent scans available at which time it is known that she had progressive disease. 5-FU was discontinued and CPT-11 was commenced for treatment of her disease Patient 16 began continuous infusion of 5-FU approximately 18 months post therapy. This patient had both liver and pulmonary lesions which appeared to decrease after iniation of 5-FU. However, there was only one scan available and it indicated a from approximately 185 cm to 117 cm (only a 37% decrease which is less 50% decrease criterion set) and there was no confirmatory scan.

Two other patients, 6 and 14, had stable disease for approximately 15 and 9 months, respectively, on their second 5-FU regimen. It should be noted that this period of stable disease is significantly longer in Patient 6 than the period of stable disease observed during the initial 5-FU treatment.

Patient 3 had progressive disease post therapy, while patients 31 and 32 appeared to have stable disease.

It should be noted that 3 additional patients received 5-FU after therapy, but not before therapy. These patients are believed to have stable disease following chemotherapy. Since this data is anecdotal, it cannot be determined with certainly that the therapy promoted the activity of the chemotherapeutics; however, based on the other data reported above, it would appear reasonable to assume that such stable disease can be attributable, at least in part, to such combination of adoptive cellular therapy and chemotherapy.

What is claimed is:

1. A method for improving the activity of cancer chemotherapeutic agents which comprises:
   (a) combining said chemotherapeutic agent with one or more of
      (i) lymph node lymphocytes which have been cultured under mitogenic stimulation conditions, or
      (ii) supernatant of said mitogenically stimulated cultured lymph node lymphocytes,
   wherein said lymph node lymphocytes that are cultured under said mitogenic stimulation conditions are cancer patient excised lymph node lymphocytes enriched in tumor reactive cells, and
   (b) administering such combination to said cancer patient.

2. The method of claim 1, wherein said excised lymph node lymphocytes are cultured in the presence of Interleukin-2 and anti-CD3 monoclonal antibody.

3. The method of claim 2, wherein said culturing further includes a tumor-associated glycoprotein (TAG) antigen.

4. The method of claim 2, wherein said culturing further includes neoplastic tissue comprising one or more of autologous neoplastic tissue or allogeneic neoplastic tissue.

5. The method of claim 4, wherein said neoplastic tissue has been inactivated prior to said culturing.

6. The method of claim 5, wherein said inactivation comprises radiation.

7. The method of claim 2, wherein the amount of Interleukin-2 ranges from between about 10 and 500 U/ml and the proportion of anti-CD3 monoclonal antibody ranges from between about 10 and 500 ng/ml.

8. The method of claim 4, wherein said culturing includes the use of serum-free media.

9. The method of claim 1, wherein said chemotherapeutic agents are administered after, or both before and after, said supernatant or said cultured lymph node lymphocytes are administered to said cancer patient.

10. The method of claim 1, wherein said cancer patient excised lymph node lymphocytes enriched in tumor reactive cells are cultured more than once under mitogenic stimulation conditions.

11. A method for improving the treatment of a cancer patient which is undergoing chemotherapeutic treatment with a chemotherapeutic agent, which comprises: co-administering said chemotherapeutic agent to said patient along with one or more of:
   (i) lymph node lymphocytes which have been cultured under mitogenic stimulation conditions, or
   (ii) supernatant of said mitogenically stimulated cultured lymph node lymphocytes,
   wherein said lymph node lymphocytes that are cultured under said mitogenic stimulation conditions are cancer patient excised lymph node lymphocytes enriched in tumor reactive cells.

12. The method of claim 11, wherein said excised lymph node lymphocytes are cultured in the presence of Interleukin-2 and anti-CD3 monoclonal antibody.

13. The method of claim 12, wherein said culturing further includes a tumor-associated glycoprotein (TAG) antigen.

14. The method of claim 12, wherein said culturing further includes neoplastic tissue comprising one or more of autologous neoplastic tissue or allogeneic neoplastic tissue.

15. The method of claim 14, wherein said neoplastic tissue has been inactivated prior to said culturing.

16. The method of claim 15, wherein said inactivation comprises radiation.

17. The method of claim 12, wherein the amount of Interleukin-2 ranges from between about 10 and 500 U/ml and the proportion of anti-CD3 monoclonal antibody ranges from between about 10 and 500 ng/ml.

18. The method of claim 14, wherein said culturing includes the use of serum-free media.

19. The method of claim 11, wherein co-administering includes administering said chemotherapeutic agents after, or both before and after, said supernatant or said cultured lymph node lymphocytes are administered.

20. The method of claim 11, wherein said cancer patient excised lymph node lymphocytes enriched in tumor reactive cells are cultured more than once under mitogenic stimulation conditions.

* * * * *

UNITED STATES PATENT AND TRADEMARK OFFICE
CERTIFICATE OF CORRECTION

PATENT NO.    : 6,093,381
DATED         : July 25, 2000
INVENTOR(S)   : Pierre L. Triozzi, et al It is certified that error appears in the above-identified patent and that said Letters Patent is hereby corrected as shown below:

Title page,
Item [73] should read -- Ohio State University Research Foundation, The, Columbus, Ohio --

Signed and Sealed this

Thirtieth Day of October, 2001

Attest:

*Nicholas P. Godici*

NICHOLAS P. GODICI
*Attesting Officer*  *Acting Director of the United States Patent and Trademark Office*

SEQUENCE LISTING

```
<160> NUMBER OF SEQ ID NOS: 4

<210> SEQ ID NO 1
<211> LENGTH: 20
<212> TYPE: DNA
<213> ORGANISM: Homo sapiens

<400> SEQUENCE: 1
atcgtgaggg cagcaaagga                                              20

<210> SEQ ID NO 2
<211> LENGTH: 18
<212> TYPE: DNA
<213> ORGANISM: Homo sapiens

<400> SEQUENCE: 2
gtggacaggc ggtgagca                                                18

<210> SEQ ID NO 3
<211> LENGTH: 18
<212> TYPE: DNA
<213> ORGANISM: Homo sapiens

<400> SEQUENCE: 3
ccctctgctg acaaccaa                                                18

<210> SEQ ID NO 4
<211> LENGTH: 20
```

-continued

```
<212> TYPE: DNA
<213> ORGANISM: Homo sapiens

<400> SEQUENCE: 4
ccccaaaatg cctccactgg                                           20
```